(12) United States Patent
Govindan et al.

(10) Patent No.: US 6,558,669 B1
(45) Date of Patent: May 6, 2003

(54) STABLE RADIOIODINE CONJUGATES AND METHODS FOR THEIR SYNTHESIS

(75) Inventors: Serengulam V. Govindan, Summit, NJ (US); Gary L. Griffiths, Morristown, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 810 days.

(21) Appl. No.: 08/919,477

(22) Filed: Aug. 28, 1997

Related U.S. Application Data

(60) Provisional application No. 60/024,738, filed on Aug. 28, 1996.

(51) Int. Cl.$^7$ ............................ C07K 5/06; A61K 39/44
(52) U.S. Cl. ................. 424/178.1; 424/179.1; 530/324; 530/345; 530/391.1; 530/391.3; 514/12; 436/512; 436/536
(58) Field of Search ................... 530/345, 324, 530/391.1, 391.3; 514/12; 424/178.1, 179.1; 436/512, 536

(56) References Cited

U.S. PATENT DOCUMENTS

| | | | |
|---|---|---|---|
| 5,273,738 A | * 12/1993 | Matthews et al. | ............ 424/1.1 |
| 5,274,076 A | 12/1993 | Wada et al. | ................ 530/330 |

FOREIGN PATENT DOCUMENTS

| | | |
|---|---|---|
| EP | 0 419 387 | 3/1991 |
| EP | 0 492 478 | 7/1992 |
| GB | 2 109 407 | 6/1983 |

OTHER PUBLICATIONS

Dumas et al., Biochim. et. Biophys. Acta, vol. 293, pp. 36–47, 1973.*
C. Paul Bianchi, Chemical Abstracts, 1–Pharmacology, vol. 1, (1988), pp 1, 404–405.
Stein et al., "Effects of Radiolabeling Monoclonal Antibodies with A Residualizing Iodine Radiolabel On The Accretion Of Radioisotope In Tumors", Cancer Research, vol. 55(14):3132–3139, (1995).
Deys et al., "Comparative Targeting Of Human Colon–Carcinoma Multicell Spheroids using One– and Two– step (Bispecific Antibody) Techniques", Chemical Abstracts, vol. 125(23):883–891, (1996).
David M. Goldenberg, "Monoclonal Antibodies in Cancer Detection and Therapy", The American Journal of Medicine, vol. 94, pp. 297–312, Mar. 1993.
Jeffrey L. Strobel, et al., "I–Glycocojugate Labels for Identifying Sites of Protein Catabolism in Vivo: Effect of Structure and Chemistry of Coupling to Protein on Label Entrapment in Cells after Protein Degradation", Archives of Biochemistry and Biophysics, vol. 240, No. 2, pp. 635–645, Aug. 1985.

F. Nicholas Franano, et al., "Metabolism of Receptor Targeted $^{111}$In–DTPA–Glycoproteins: Identification of $^{111}$In–DTPA–68–lysine as the Primary Metabolic and Excretory Product", Nucl. Med. Biol. vol. 21, No. 8, pp. 1023–1034, 1994.
Seham A. Ali, et al., "Improving the Tumor Retention of Radioiodinated Antibody: Aryl Carbohydrate Adducts", Cancer Research (Suppl.), vol. 50, pp. 783–788, Feb. 1990.
Elizabeth J. Pawlak–Byczkowska, et al., "Two New Monoclonal Antibodies, EPB–1 and EPB–2, Reactive with Human Lymphoma", Cancer Research, vol. 49, pp. 4568–4577, Aug. 1989.
D. Scott Wilbur, et al., "Development of a Stable Radioiodinating Reagent to Label Monoclonal Antibodies for Radiotherapy for Cancer", The Journal of Nuclear Medicine, vol. 30, pp. 216–226, 1989.
Rhona Stein, et al., "Murine Monoclonal Antibodies Raised against Human Non–Small Cell Carcinoma of the Lung: Specificity and Tumor Targeting", Cancer Research, vol. 50, pp. 1330–1336, Feb. 1990.
Rhona Stein, et al., "Murine Monoclonal Antibodies Raised against Human Non–Small Cell Carcinoma of the Lung: Specificity and Tumor Targeting", Cancer Research, vol. 50, pp. 1330–1336, Feb. 1990.
Rhona Stein, et al., "Effects of Radiolabeling Monoclonal Antibodies with a Residualizing Iodine Radiolabel on the Accretion of Radioisotrope in Tumors", Cancer Research, vol. 55, pp. 3132–3139, Jul. 1995.
Serengulam V. Govindan, et al., "Thiolations, $^{99m}$Tc Labelings, and Animal In Vivo Biodistributions of Divalent Monoclonal Antibody Fragments", Articles: Bioconjugate Chem., vol. 7, pp. 290–297, 1996.
Hans J. Hansen, et al., "Characterization of Second–Generation Monoclonal Antibodies Against Carcinoembryonic Antigen", Cancer, vol. 71, No. 11, pp. 3478–3485, Jun. 1993.

* cited by examiner

Primary Examiner—Bennett Celsa
(74) Attorney, Agent, or Firm—Foley & Lardner

(57) ABSTRACT

Methods are described for conjugating radioiodinated peptides or carbohydrate structures to proteins with improved yields and qualities of conjugates. In one method, specially designed radioiodinated bifunctional peptides containing nonmetabolizable amide bonds are coupled to antibodies. In a second method, radioiodinated nonmetabolizable bifunctional peptides, which also contain aminopolycarboxylates, are coupled to antibodies. In a third method, radioiodinated bifunctional aminopolycarboxylates are coupled to antibodies. In a fourth method, a hydrazide-appended antibody is coupled to a radioiodinated carbohydrate or a thiolated antibody is coupled to a hydrazide-appended and radioiodinated carbohydrate. In a fifth method a monoderivatized cyanuric chloride is used to conjugate thiolated antibody. Radioiodinated residualizing antibody conjugates made by these methods are particularly stable in vivo and are suitable for radioimmunodetection and radioimmunotherapy.

11 Claims, No Drawings

STABLE RADIOIODINE CONJUGATES AND METHODS FOR THEIR SYNTHESIS

This application claims the benefit of U.S. Provisional Application No. 60/024,738 filed on Aug. 28, 1996.

FIELD OF THE INVENTION

This invention relates to the preparation of reagents used in radioimmunodetection and radioimmunotherapy and specifically to the preparation of radioiodine labeled conjugates having enhanced stability in vivo and enhanced retention at tumor sites.

BACKGROUND OF THE INVENTION

Radioiodinated monoclonal antibodies are important for the diagnosis and therapy of cancer as summarized by Goldenberg in *Amer. J. Med.* 94: 297–312 (1993). A number of methods have been developed over the last thirty years to chemically introduce radioiodine into monoclonal and polyclonal antibodies for these uses. Iodine is preferred as a radiolabel in these applications because the chemistry used for radioiodination of protein is relatively easy, radioiodine has useful physical decay characteristics, and isotopes of iodine are commercially available.

Among useful iodine isotopes are Iodine-124, which has been used to radiolabel antibodies as described by Pentlow et al., *Journal of Nuclear Medicine*, 37: 1557–62 (1996), and Iodine-125, which has been used for detection using an intraoperative probe as described by Martin et al., *Cancer Investigation*, 14: 560–71 (1996). In the context of using these iodine isotopes, one concern is the long circulation time of radioiodinated antibodies, which leads to high background radiation. The high background problem is compounded by the loss of radioiodine from target cells, when standard radioiodination methods are used. A poor target to non-target ratio of delivered iodine often results from the high background and radioiodine loss problems. Accordingly, a principal aim in the art is to improve the target to non-target ratio.

Iodine-125 has been proposed for therapy purposes because of its cascade Auger electrons as described by Aronsson et al., *Nuclear Medicine and biology*, 20: 133–44 (1993). Clearly, optimum use of a long-lived [$t_{1/2}$, 60 days] low energy-emitting nuclide demands that intracellular target retention be achieved; which is not possible with conventional radioiodination methods.

Various chemistries have been developed to link iodine to antibodies that target cancer cells. These chemistries have been reviewed by Wilbur, *Bioconjugate Chemistry* 3: 433–70 (1992). The most common linking procedure has been to prepare in situ an electrophilic radioiodine species to react with a functional group on an antibody. Reagents such as chloramine T and iodogen have been employed to generate electrophilic iodine. A tyrosine group on protein is usually the site of iodination. However, the presence of a harsh oxidant or reductant may lead to structural impairment of an antibody. For this reason, an alternative approach is to iodinate a small organic molecule and couple the pure iodinated species to antibody. N-Succinimidyl 3-(3-iodo-4-hydroxyphenyl) propionate (Bolton-Hunter reagent) is an example of the latter category. These and other methods have been reviewed by Wilbur (Id).

A major drawback with using the foregoing radioiodination schemes is the phenomenon of in vivo deiodination. As a result of antibody internalization and lysosomal processing in vivo, a labelled protein is degraded to small peptides, and its radioiodine is released from the cell in the form of iodotyrosine or as iodine attached to a low molecular weight peptide fragment. These findings have been reported by Geissler et al., *Cancer Research* 52: 2907–2915 (1992) and Axworthy et al., *J. Nucl. Med.* 30: 793 (1989). Such in vivo removal of radioiodine from target cells has a profound bearing on the use of iodine isotopes for radiodiagnosis and radiotherapy. Discrimination between tumor and non-tumor that is relevant to diagnosis and therapy, and the prolonged retention of isotope on a tumor cell, relevant to radiotherapy, are severely compromised by the occurrence of in vivo deiodination. This is readily appreciated if one considers the 8-day half-life of iodine-131, which is widely used for radioimmunotherapy investigations. If antibodies radioiodinated with this isotope are metabolized with consequent removal of the isotope from the target cells within the first 24–120 h post-injection of the reagent, the advantage of the lengthy half-life of this isotope for therapy is lost. That is, the useful half-life of this isotope is not exploited in a prolonged tumoricidal effect because of the above-described drawback of conventional radioiodination chemistry.

In contrast to this drawback of conventional chemistry, the action of in vivo deiodinases in releasing iodine in the form of molecular iodine from the cell is less significant to the problem of optimizing the target to non-target ratio of radioisotope accumulation. Workers in this field have attempted to prepare iodinated proteins that do not 'deiodinate' by the action of in vivo deiodinases as reviewed by Wilbur et al., *Journal of Nuclear Medicine*, 30: 216–26 (1989). But these attempts have failed to show improvement in cellular retention of radioiodine. The reason for these failures is that, contrary to what was expected, the metabolic clearance of intact iodotyrosine was more important to clearance of isotope than was the deiodination of tyrosine to liberate radioiodine.

One way to overcome the unacceptably fast release of radioiodine from conjugate is to attach iodine to non-metabolizable carbohydrate and to conjugate the resultant entity to antibodies. After antibody catabolism within a tumor cell, the radioiodine remains stably attached to the carbohydrate and thus is trapped inside the cell. These carbohydrate labels, referred to as 'residualizing labels', are exemplified by Strobel et al., *Arch. Biochem. Biophys* 240: 635–45 (1985) and Ali et al., *Cancer Research* (suppl) 50: 783s–88s (1990). However, these methods, when applied to the labelling of monoclonal antibodies (Mabs), suffer from one or both of the following drawbacks: (1) Very low radiolabeling yields (3–6 %) and (2) formation of aggregates (up to 20%). Low conjugation yield necessitates handling a large amount of radioactive iodine to incorporate sufficient radioactive label in antibody. This approach causes a radiation safety concern as well as wastage of most of the unusable radioactivity. As a result, the specific activity achieved by this method suffers. Furthermore, aggregate formation can lead to reduced tumor uptake and will lead to enhanced liver uptake, and thereby impair the effectiveness of the radiolabel method. The full advantage of using residualizing labels for radioimmunodetection and radioimmunotherapy cannot be realized unless progress can be made to limit the twin problems of poor radiolabeling yield and aggregate formation when using carbohydrate-based reagents. Using novel substrates and methodologies to address these issues is another aspect of this invention.

One well known approach to this problem is to label the antibody with a radiometal ion such as indium-111 or an isotope of yttrium, using a bifunctional aminopolycarboxylate ligand such as bifunctional EDTA or bifunctional LDTPA. These radiolabelled conjugates exhibit prolonged retention of radiometal in tumor as exemplified in vivo animal experiments by Stein et al., *Cancer Research* 55: 3132–39 (1995). That is, radiometal ions chelated to aminopolycarboxylates also behave, in vivo, as residualizing labels. Thus, the problem of residualization generally applies to techniques that use these labels as well.

The prior art has addressed the issue of residualizing iodine labels by using non-metabolizable sugars to which an iodinatable group is attached. An iodinatable group such as tyramine is reductively coupled to the carbohydrate, so that there is no metabolizable peptide bond between tyramine and the sugar entity. There are two main problems encountered with these prior art methods. These are in the antibody-coupling steps. One method, that of Strobel et al. (see above), uses a carbohydrate-adduct derived from lactose, and couples proteins and antibodies to the same by first oxidizing the galactose portion of such adducts with galactose oxidase. Usually poor overall yield (3–6%) is obtained, as described by Stein et al. *Cancer Research*, 55: 3132–3139, (1995). Furthermore, lactose is an inefficient substrate for galactose oxidase. In examining a number of galactose-containing carbohydrate derivatives for their ability to be oxidized by this enzyme, Avigad et al. (*J. Biol. Chem* 237: 2736–2743, (1962)), determined that lactose had less than half the affinity of D-galactose for galactose oxidase, and was oxidized fifty times slower compared to galactose. This inefficient step therefore contributes to overall reduced radioisotope incorporation into antibodies.

Another approach involved in coupling to antibodies does not make use of any special property such as the ability of the carbohydrate to be selectively derivatized by an enzyme (such as galactose oxidase oxidation involving galactose moiety), but makes use of cyanuric chloride as the cross-linker to link both the iodinated carbohydrate and antibody. This approach has the serious problem of generating antibody aggregates.

Cyanuric chloride has been used to form conjugates but unfortunately this reagent contains three reactive chlorines and consequently forms aggregates. Another factor involved in aggregate formation is the presence of multiple amino residues in antibodies that can bind to the residualizing agent and/or coupling reagent, particularly with carbohydrate residualizing agents that couple to protein by reductive amination. Such multiple binding causes aggregates to form, and results in low specific activity of radiolabel in the prepared conjugate mixture. Accordingly, coupling agents are needed that do not cause aggregate formation.

SUMMARY OF THE INVENTION

The present invention solves the above-identified problems by providing preparation methods and compositions of iodinatable peptides consisting of unnatural D-amino acid components. The radioiodinated versions of these conjugates are used to label antibodies and produce residualizing labels.

The present invention also is directed to the design of bifunctional iodinatable aminopolycarboxylate adducts wherein the iodinatable group is attached to the said aminopolycarboxylate unit via a non-metabolizable peptide bond. The adducts are radioiodinated and conjugated to Mabs or their fragments, and thereby introduce residualizing label into biospecific Mabs.

The present invention additionally is directed toward the design of new methodologies to improve yields in the radioiodination of monoclonal antibodies using carbohydrate-based reagents.

The present invention is further directed to the design of carbohydrate-based reagents which improve the quality of residualizing label-antibody conjugates (with minimal aggregation) and thereby decrease non-target accumulation (especially in liver) of the label in vivo.

The present invention is also directed toward the ready attachment of such residualizing radioiodine labels to targeting vectors, including proteins such as monoclonal antibodies, fragments and constructs thereof.

In one embodiment, nonmetabolizable and radioiodinated peptides are used for labeling antibodies so that the radioactivity is residualized in vivo. These specially designed hydrophilic peptides preferably have a molecular weight of more than 500 (i.e. 5 amino acid residues or more). More preferably, the peptide has a molecular weight of between 1000 and 4000 (10 to 40 amino acid residues) although in some cases more than 40 amino acids are acceptable. A hydrophilic peptide in the context used here means that the peptide contains polar amino acid units that are charged, such as aspartic acid, glutamic acid, lysine and arginine or that are polar, such as serine and threonine. The presence of multiple hydrophilic acid groups from these residues and their nonmetabolizable peptide bonds allow residualization of the radiolabel after antibody catabolism by lysosomes. Most preferred in this context are acidic amino acid residues such as aspartic acid.

D-amino acids comprise the peptide between the site of attachment of the peptide to an antibody and a radioactive iodine that is bound to a tyrosine or tyramine. Most particularly, within this region, no two adjacent amino acids are L-amino acids. Glycine in this context is an L-amino acid. By using D-amino acids in this way, the peptide bonds that connect the radioactive iodine to the antibody cannot be hydrolyzed in a lysosome.

In a second embodiment, a bifunctional aminopolycarboxylate system containing an iodinatable group is prepared by first synthesizing a peptide unit consisting of two differentially protected amino groups and unnatural D-amino acid units in the peptide mer. Sequential elaboration of the amino groups by adding an aminopolycarboxylate unit and then adding a protein cross linker completes the synthesis of the bifunctional aminocarboxylate. The peptide contains one or more unnatural D-tyrosine units. The amino acid units of the peptide are attached via non-metabolizable amide bonds. The antibody-binding group can be an amino residue (for site-specific attachments to oxidized carbohydrate of MAbs), an imidate or isothiocyanate (attachable to lysine groups of proteins), maleimide, bromo- or iodoacetamide residue (specific to thiols on Mabs) and the like. The number of amino acid units in the peptide is two to ten, preferably three, of which at least one is D-tyrosine. The amino acid(s) immediately following the last D-tyrosine unit, and which are used to introduce antibody-binding cross-linkers, can be natural L-amino acids. The aminopolycarboxylate unit can be iminodiacetic acid, nitrilotriacetic acid, EDTA (ethylenediaminetetraacetic acid), DTPA (diethylenetriaminetetraacetic acid), TTHA (triethylenetetraminehexaacetic acid), DOTA (1,4,7,10-tetraaza cyclododecane N,N',N'',N'''-tetraacetic acid) or various backbone-substituted versions thereof, such as, for example, isothiocyanatobenzyl-EDTA/DTPA/TTHA/DOTA, among numerous other aminopolycarboxylates and their derivatives which can be readily envisaged.

In a third embodiment, the bifunctional iodinatable aminopolycarboxylate is derived by attaching a tyramine group and an antibody-binding group to the is aminopolycarboxylate. No protease-susceptible bond is involved in these structures. Alternatively, aminopolycarboxylates, backbone-substituted with an antibody-binding unit, are converted to corresponding dianhydrides which are then reacted with D-tyrosine to obtain an entity that contains two D-tyrosine residues. Since the amide bond(s) between the bifunctional aminopolycarboxylate and D-tyrosine will not be recognized by proteases, these constitute a different version of residualizing iodine labels.

One key feature in all of these systems is that the iodinated D-tyrosine moiety will be resistant toward deiodinases. This possibility is described by Dumas et al., *Biochem. Biophys. Acta* 293: 36–47 (1973).

In a fourth embodiment, a carbohydrate-based residualizing label is designed using a disaccharide which contains a galactose unit and which can be oxidized readily with galactose oxidase. This embodiment is exemplified by a preparation derived from melibiose. Another example is provided wherein the carbohydrate-based residualizing label is prepared which already contains an antibody-binding group. Yet another aspect in this regard involves using hydrazide-appended antibodies for reaction with iodinated and derivatized carbohydrate.

In a fifth embodiment, a radioiodinated carbohydrate is allowed to react with a cyanuric chloride derivative which in turn is already derivatized to possess antibody-binding moiety.

Methods of the invention provide greater efficiencies of antibody labeling with residualizing iodine labels. The methods also provide higher quality stable radioiodine conjugate preparations having a low aggregate content. Other objects and advantages will become apparent from the following detailed description.

DETAILED DESCRIPTION

The present invention solves the problems of poor labeling efficiency and aggregate formation reported in the carbohydrate-based prior art in two general ways. In the first way, a new method is provided that allows oxidation of the galactose-containing carbohydrate-tyramine (or D-tyrosine) adduct by galactose oxidase. The invention achieves this by using melibiose as the carbohydrate in the adduct. The affinity of melibiose for galactose oxidase is five times as high as that of galactose and ten-times as high compared to the affinity of lactose for galactose oxidase. Furthermore, melibiose is oxidized at a rate comparable to galactose. Consequently, this method of the invention enhances the overall process yield obtained in the oxidation step. Overall incorporations of 18.7–20.7% (see Example-9) have been achieved for the radioiodination of antibody using radioiodinated and oxidized (oxidation using galactose oxidase) dimelibiitoltyramine of the present invention. These incorporations are five-to-ten fold higher than yields observed in the radioiodination of the same antibody, using radioiodinated and oxidized dilactitoltyramine. An advantage of the present invention in this regard lies in utilizing a substrate (dimelibiitoltyramine) which is oxidized readily by galactose oxidase. An additional invention in this context involves the use of hydrazide-appended antibodies which results in enhanced yield in the step of reductive coupling of carbohydrate addend to proteins.

The second way that the invention solves the prior art problems mentioned above is to improve the quality of iodinated antibody conjugate prepared by cyanuric chloride-mediated protein-carbohydrate coupling. This is achieved two ways: (1) by introducing one, or a limited number of more reactive hydrazide residues into an antibody that reacts preferentially with the coupling reagent, instead of the more numerous protein primary amine residues; and (2) by using cyanuric dichloride derivatives to couple antibody to residualizing label. As used in the invention, monosubstituted cyanuric chloride, prepared under non-aqueous conditions, carries a thiol-reactive entity such as maleimide, and is used for coupling to thiolated antibody. The second chlorine of this cyanuric dichloride is used to react with a phenolic hydroxyl group, such as that from a tyramine residue, while the thiol group of thiolated antibody reacts with maleimide group in a subsequent step. The third chlorine is unreactive, and is not a factor. Aggregate formation is therefore minimized and specific activity of the prepared conjugates is improved.

According to one aspect of the invention a radioisotope of iodine is attached in a non-metabolizable manner to a substrate. The iodine then becomes trapped within the acidic environment of lysosomes after antibody catabolism. The consequent prolonged retention of radioiodine within a target cell such as a tumor cell facilitates target organ dosimetry and enhanced target to non-target discrimination. In the context of tumor targeting this enhancement allows more effective radiodiagnosis and radiotherapy.

Another aspect of the invention is a new class of peptide-based residualizing labels. These residualizing labels address problems encountered in the use of carbohydrate-based iodine labels.

The use of peptide-based residualizing labels involves peptides consisting of one or more unnatural D-tyrosine units that are bonded to other unnatural amino acids. These peptides preferably contain hydrophilic amino acids such as D-aspartic acid and D-glutamic acid units for increased hydrophilicity, and are of at least 5 amino acid residues in size. The amino terminal residue of these peptides can be an L- or D-amino acid, provided that if an L-amino acid, it is not directly attached to a tyrosine, and can be attached to a protein-binding cross linker for later attachment to an antibody. Once radioiodinated and coupled to antibody, the iodinated peptide unit is residualized within a cell lysosome after attachment to a cell surface via binding and processing of the associated antibody. The presence of non-metabolizable amide bonds, hydrophilic amino acid residues such as charged aspartic acid residues and glutamic acid residues, and a size greater than 4 amino acid residues collectively enable such residualization. Most preferred in this context is the use of aspartic acid residues for the peptide.

The conjugate's structure can be varied by using D-lysine at the peptide carboxyl terminus. This provides an ε-amine group for attaching an aminopolycarboxylate such as nitrilotriacetic acid (NTA), ethylenediaminetetraacetic acid (EDTA), diethylenetriaminepentaacetic acid (DTPA) or triethylenetetraminehexaacetic acid (TTHA). In this embodiment, the ε-amine at the carboxyl end and the amine at the amine terminus are differentially, protected for attaching an amino-polycarboxylate and a cross-linker at designated loci. In this variation of the invention, D-aspartic acids in the peptide are optionally substituted with other amino acids. Yet another variation is the rational design of aminopolycarboxylate systems which contain a radioiodinatable group such as tyramine as well as an antibody-binding moiety.

Products of the present invention deal with structural aspects which confer enhanced stability after the antibody is internalized and processed. It is this antibody processing that leads to diminished retention of radioiodine in tumor, which is exacerbated with internalizing antibodies. Our invention addresses this issue by the design of a non-metabolizable peptide template which is also attached to aminopolycarboxylate and an iodinatable entity. By attaching polar groups such as DTPA to D-lysine which in turn is attached to D-tyrosine which is coupled to a protein binding moiety, the invention ensures that the entire piece of aminocarboxylate-D-lysine-[I-125]-D-tyrosine portion will be trapped in lysosomes, after antibody processing, by virtue of the presence of protease-resistant peptide bonds, hydrophilic nature and the size. This is in contrast to iodotyrosine, the catabolite of conventionally radioiodinated antibody, which readily escapes from the lysosomes and causes reduced radioactivity retention at the tumor sites.

Definitions

In the description that follows, a number of terms are utilized extensively. Definitions are provided here to facilitate understanding of the invention.

Phosphate buffer. As used herein, "phosphate buffer" refers to an aqueous solution of 0.1 M sodium phosphate that is adjusted to a Ph between 6.0 and 7.5.

Antibody. As used herein, "antibody" includes monoclonal antibodies, such as murine, chimeric, humanized or human antibodies, as well as antigen-binding fragments thereof. Such fragments include Fab, Fab', F(ab)$_2$, and F(ab')$_2$ which lack the Fc fragment of an intact antibody. Such fragments also include isolated fragments consisting of the light chain variable region, "Fv" fragments consisting of the variable regions of the heavy and light chains, (sFv')2 fragments (see, for example: Tai et al., *Cancer Research Supplement*, 55:5983–5989, 1995), and recombinant single chain polypeptide molecules in which light and heavy variable regions are connected by a peptide linker.

Radioiodine-antibody conjugate. As used herein, a radioiodine-antibody conjugate is a molecule comprising at least one residualizing label and an antibody. A radioiodine-antibody conjugate retains the immunoreactivity of the antibody, i.e., the antibody moiety has roughly the same, or only slightly reduced, ability to bind antigen after conjugation compared to binding before conjugation with the residualizing label.

Residualizing label. "Residualizing label" is a radiolabel that is covalently attached to protein and has been designed to remain entrapped within lysosomes or another subcellular compartment following degradation of the carrier protein. Generally, residualizing labels are synthesized from molecules which themselves are not readily degraded in lysosomes. In general, these tracers have been radioactive carbohydrates or metal chelates of aminopolycarboxylates such as DTPA.

Any non-metabolizable carbohydrate is suitable for the present invention. Dimelibiitoltyramine (DMT) and melibiitoltyramine (MT) are some examples in this category. Bifunctional DTPA (or EDTA), either alone or as a D-tyrosine appended substrate, exemplifies the category of aminopolycarboxylates.

Aggregate. As used herein, an "aggregate" is a molecular complex comprising at least one extra polypeptide in addition to the desired antibody. The extra polypeptide is coupled directly or indirectly to the antibody by covalent means. Examples of aggregates are dimers, trimers and other multimers of the antibody. Macromolecular complexes comprised of more than one residualizing label per antibody can be considered aggregates if by virtue of excessive labeling of antibody by residualizing label, the antibody binding activity is compromised. But the labeling of an antibody by multiple residualizing labels is often desired as a means to increase the specific radioactivity of the prepared antibody conjugate.

Five embodiments of the present invention are shown in SCHEMES I–VII below and are described seriatim.

SCHEME I

ABG-[CL]-AA-[(D)-AA]$_m$-[(D)Tyr]$_n$-(D)-Lys-OH

Where m and n are each integers and m+n=4–40, AA represents an amino acid, D denotes a D-amino acid, CL is a cross linker and ABG is an antibody-binding group. The design of a peptide containing one or more D-tyrosine residues, one or more hydrophilic amino acids such as D-aspartic acid and other amino acids is achieved by using a resin. The Fmoc protected first amino acid (optionally shown as D-lysine) is anchored via its carboxyl end to a resin support such as from a chlorotrityl-chloride resin. The peptide is elaborated by sequential addition of amino acids, each amine is protected by a Fmoc group and the carboxylic acid is activated. After forming each amide bond, the Fmoc group is removed. This removal allows coupling to the next carboxyl-activated Fmoc-protected D-amino acid. The assembly of peptides is thus a straightforward procedure. After liberating the final peptide from the solid support, the amine terminus is attached to a suitable heterobifunctional or homobifunctional cross-linker. Many of these cross-linkers are commercially available. One or more hydrophilic amino acids such as aspartic acid are introduced to increase the hydrophilicity of the peptide. The peptide thus formed has a minimum size of 5 amino acids. A metabolically stable D-tyrosine-containing hydrophilic peptide made in accordance with the invention is useful as a residualizing iodine label.

SCHEME II

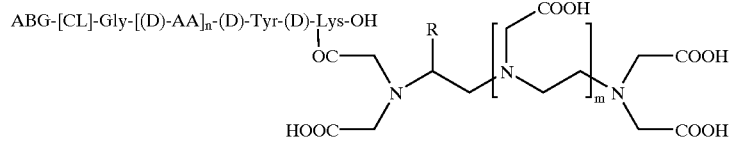

A variant of the above theme is to prepare a peptide that contains a D-lysine at its carboxyl terminus and attach the ε-amino group of this lysine to an aminopolycarboxylate such as, for example, EDTA, DTPA, and the like. In the general structure shown in SCHEME II, m is an integer having a value of 0, 1 or 2. In the peptide portion, the letter D denotes D amino acid, AA stands for amino acid and n is an integer of from 2 to 40. The amine terminus, shown here as glycine, is attached to a cross-linker CL which terminates

SCHEME III

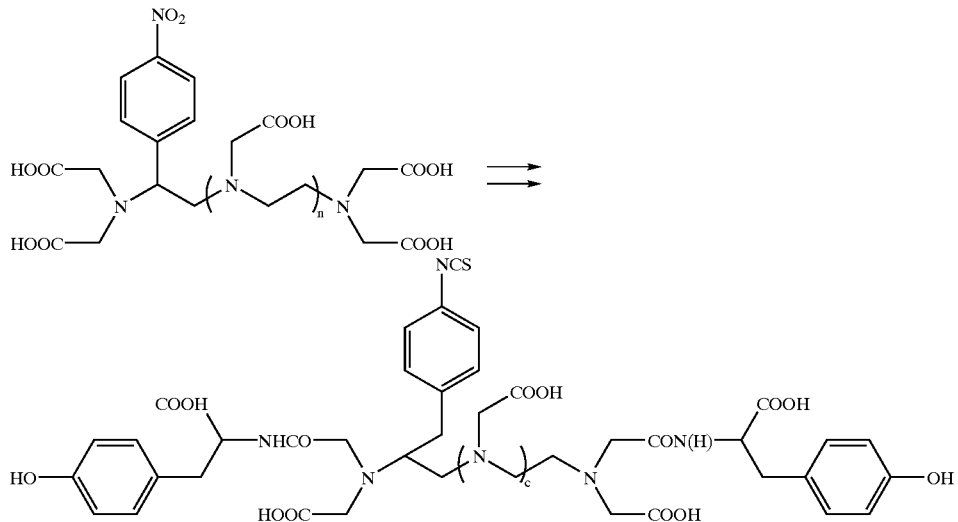

in an antibody-binding group ABG. The latter can be any protein binding group such as a maleimide, halacetamide, isothiocyanate, succinimide ester, imidate ester, and the like. Substituent R in the aminopolycarboxylate is hydrogen or a group such as 4-isothiocyanatobenzyl to which the peptide portion is attachable. The mode of attachment of DTPA, for example, is via an amide bond (as shown in the structure above) by reaction of the ε-amine of D-lysine with DTPA dianhydride, or via an isothiourea bonding to isothiocyanatobenzyl DTPA (with the peptide attached to R). It is known from the work of Franano et al., *Nucl. Med. Biol.* 21: 1023–34 (1994) and others that the amide bond or isothiourea bond between DTPA and ε-amine of lysine is inert (nonmetabolizable) in the lysosomes. It is also known that antibodies radiometalated by, for example, indium or yttrium via an aminopolycarboxylate such as DTPA as a metal chelator are residualized. This phenomenon, documented by Stein et al. (see above) and others, is due to the hydrophilic nature of the metal chelate as well as its charge and molecular weight, which all contribute to residualization in a lysosomal compartment. This invention uses aminopolycarboxylate on an iodinatable and nonmetabolizable peptide template as one method of producing-residualizing iodine label. To this end, D-lysine, which is coupled to an aminopolycarboxylate, is elaborated on the amino end by attaching a D-tyrosine, thus producing a totally inert adduct, which when iodinated and attached to antibodies via a cross-linker at the amine terminus of the said peptide, results in a residualizing radioiodine. When radioiodinated and coupled to a lymphoma antibody LL2 the product resembles the same antibody labeled with indium-111 in terms of retention to a lymphoma cell line in vitro, and an enhanced retention compared to the same antibody which is conventionally radioiodinated (see Example-5).

Peptides of this category can be readily synthesized on a solid support, either manually or using an automated peptide synthesizer. The number of amino acid units can be 2–40, with the provision that the DTPA anchoring amino acid is D-lysine or D-arginine or D-ornithine, and that this amino acid is directly attached to a D-tyrosine. When the peptide contains multiple D-tyrosines (which is useful for enhancing specific activities), each tyrosine is attached to D-amino acids. The amine terminus of the peptide can be glycine or an L or D amino acid, and is attached to a cross-linker for coupling to antibodies.

In the reaction sequence shown in SCHEME III, a substituted aminopolycarboxylate such as DTPA is used to couple radioiodine to antibody. A backbone-substituted DTPA such as 4-nitrobenzyl DTPA (structure on left in SCHEME III where n=0,1,2) is a logical starting point for the synthesis. A dianhydride is prepared from nitrobenzyl DTPA, and is opened with D-tyrosine under basic non-aqueous conditions in DMSO or DMF. The nitrobenzyl group in this substrate easily is converted to an isothiocyanatobenzyl group in a 2-step process of catalytic hydrogenation and reaction with thiophosgene (product structure not shown). This substrate is first radioiodinated and then coupled to antibody between pH 8–9. Although exemplified by a bifunctional DTPA as the starting material, the method is applicable to the use of bifunctional EDTA or bifunctional TTHA as a starting material.

SCHEME IV

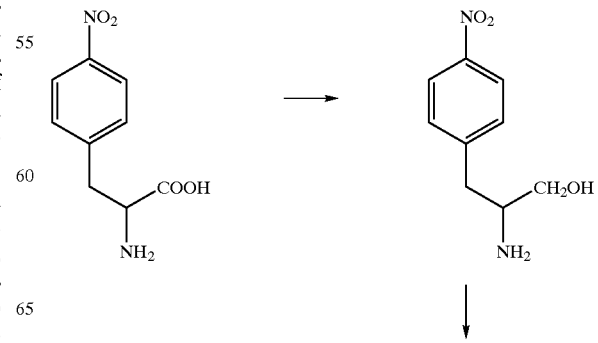

-continued

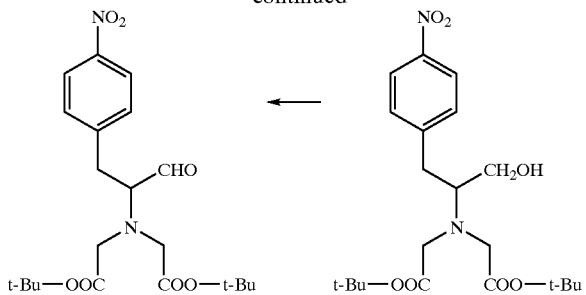

In another approach, a tyramine and an antibody-binding moiety form part of the aminopolycarboxylate structural unit. This is illustrated by the bifunctional structures N,N-bis(carboxymethyl)-N'-[2-(p-hydroxy-phenyl) ethyl]-2-[p-isothiocyanatobenzyl]ethylenediamines A and B of the reaction scheme shown. Briefly, the synthesis involves elaborating 4-nitrophenylalanine by first reducing the carboxyl group to alcohol by, for example, using borane as a reducing agent, followed by dialkylation, and oxidation of the alcohol group to an aldehyde via Sloan oxidation with oxalyl chloride in DMSO followed by reductive coupling to tyramine, and finally converting the nitrobenzyl group to an isothiocyanatobenzyl group. These residues are first radioiodinated and then coupled to antibody lysine groups or to thiolated antibodies. The presence of the basic amino groups and the carboxylic acid groups in the prepared conjugate aids residualization within the acidic lysosome environment.

SCHEME V

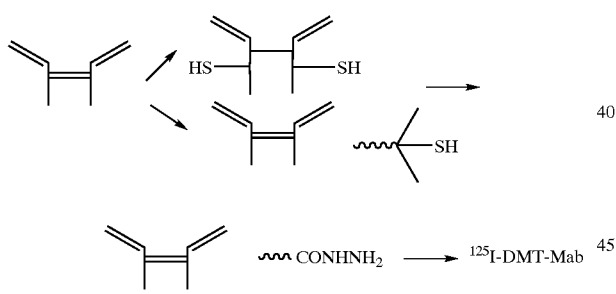

In the reaction sequence shown in SCHEME V, one or more thiol groups are introduced into an antibody such as a monoclonal antibody (Mab) by one of two illustrative methods. In the first, a disulfide bond reducing agent, such as dithiothreitol (DTT), effects either partial or complete cleavage of heavy chain disulfide bonds. Alternatively, one or more thiol groups

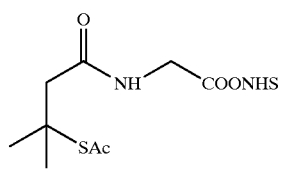

(1)

are introduced with a linker. A protected tertiary thiol is preferred, such as a succinimidyl 2-[N-(3'-methyl-3'-thioacetyl)butamidyl]acetate (1), the thioester of which is then cleaved with hydroxylamine as described by Govindan et al. in *Bioconjugate Chemistry*, 7:290–297, 1996.

The resultant thiolated antibody is linked to a hydrazide using a maleimide/hydrazide conjugate, e.g., 4-[4'-(N-maleimidyl)-phenyl]butyrylhydrazide (MPBH, 2) or 4-(N-maleimidylmethyl)cyclohexane-1-carboxyhydrazide ($M_2C_2H$, 3).

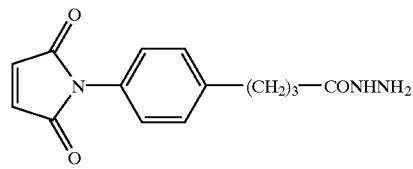

(2)

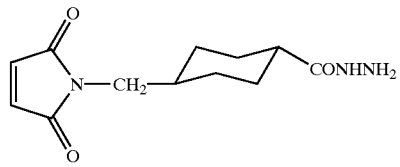

(3)

Finally, the hydrazide is coupled to a radioiodinated, carbohydrate, e.g., dimelibiitol tyramine (DMT, 4) that has been oxidized, for example by enzymatic reaction with galactose oxidase.

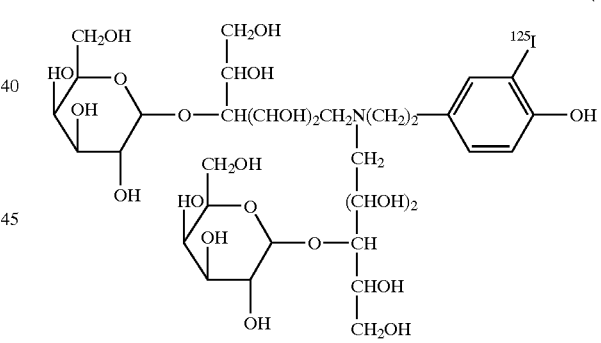

(4)

This oxidized carbohydrate optionally is further stabilized by a reductive amination reaction to form radioiodinated DMT-Mab-conjugate.

One advantage of the present invention is that, in contrast to Schiff base adducts of oxidized carbohydrates formed from simple primary amines such as those from lysine, the hydrazone conjugates according to the present invention do not require reduction of the imine (hydrazone) function for stabilization. Hydrazones are resistant to hydrolysis under physiological conditions, while Schiff bases are much more easily hydrolyzed.

SCHEME VI

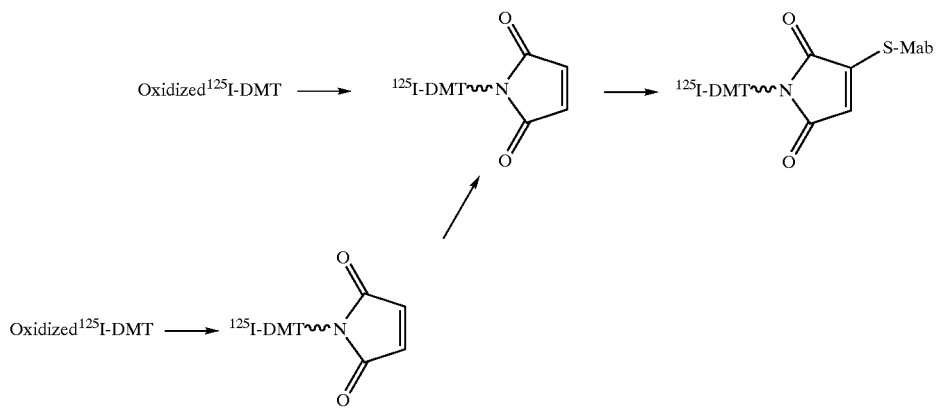

In the reaction sequence shown in SCHEME VI, an oxidized carbohydrate, e.g., DMT, couples with a maleimide/hydrazide conjugate, e.g., MPBH (2) or $M_2C_2H$ (3) to form a maleimide dimelibiitoltyramine. A maleimide group is alternatively introduced by first reductively coupling 2-aminoethylcarbamate to oxidized dimelibiitoltyramine or oxidized melibiitoltyramine, followed by deprotection of the remaining primary amino group and its further conversion to maleimide. The tyramine residue is iodinated either before or after this reaction. One or more thiol groups are introduced to an antibody by one of two methods as described above. Finally, the maleimide is coupled to the antibody to form a stable radioiodine DMT-antibody conjugate.

Oxidation with a periodate such as sodium or potassium periodate can create aldehyde functionalities on the carbohydrate, although compounds containing two or more keto or hydroxyl groups attached to adjacent carbon atoms tend to cleave between these two carbons. Periodate oxidation can cause extensive isomerization and even decomposition of a carbohydrate chain. For these reasons it is preferred to oxidize carbohydrate with an enzyme such as galactose oxidase, which can introduce one aldehyde functionality into the carbohydrate without causing other structural changes.

SCHEME VII

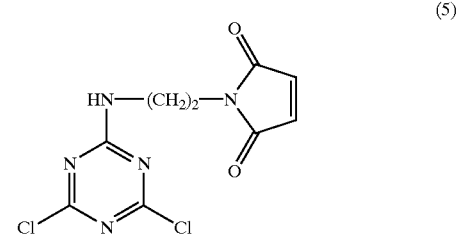

The reaction sequence of SCHEME VII shows coupling of radiolabelled tyramine carbohydrate, such as DMT (4), or MT with a substituted cyanuric chloride (CC) via displacement of a chlorine on the cyanuric dichloride. The first chlorine of cyanuric chloride is very reactive, the second chlorine of monosubstituted CC is somewhat less reactive, while the remaining chlorine in the disubstituted CC is relatively unreactive. According to one advantageous embodiment, a monosubstituted CC is prepared under non-aqueous conditions, from equimolar quantities of CC and a maleimide-containing amine, e.g. monosubstituted CC analog (CC analog 5, below).

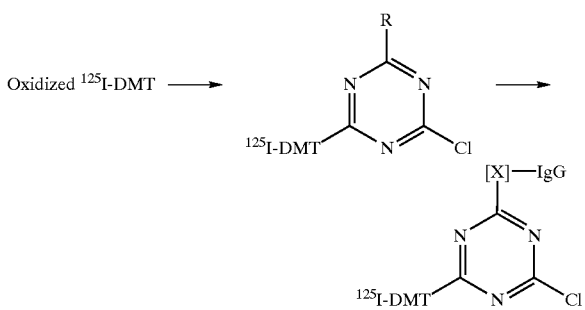

(5)

From the monosubstituted CC depicted above, only one chlorine is readily available for reaction with a radioiodinated carbohydrate such as I-125-DMT. Furthermore, the maleimide group, being thiol-reactive, can couple subsequently to a thiolated antibody. The high reactivity of thiol toward maleimide obviates low yield and aggregation problems that result from protracted reaction of antibody amine with DMT-derivatized CC.

Although an Iodine-125 (I-125) radioisotope exemplifies the embodiments shown in SCHEME I–VII, the methods of the present invention are applicable to any iodine isotope. I-123 is especially preferred for use in tumor imaging, Iodine-131 (I-131) is especially preferred for use in tumor therapy and I-125 is preferred for short-range detection of tumor margins, e.g. for intraoperative, intravascular or endoscopic procedures.

The incorporation of radioiodine into a peptide or carbohydrate of the present invention is carried out by an electrophilic substitution reaction. This reaction is fast and allows coupling in dilute solutions of radioiodine. The reaction generally requires oxidation of iodine ions to produce an electrophilic radioiodination reagent. Methods for oxidizing halide ions are well known in the art and are described by Wilbur (see above). Although the invention exemplifies sodium iodide/iodogen combinations, the method is not limited to this reagent combination.

Reactions of substituted cyanuric dichloride are preferably carried out at neutral pH. Neutral pH is defined as a pH between pH 4.5 and pH 9.5. A neutral pH between pH 6 and pH 8 is especially preferred for the invention.

Many different kinds of maleimide-hydrazides are known or can be made by the skilled artisan and are suitable for the present invention. Especially preferred are the two maleimide-hydrazides (2) and (3) shown above. Other maleimide-hydrazides can be synthesized from a maleimido N-hydroxy-succinimide ester. Representative maleimido-esters useful for this purpose are: 3-maleimidobenzoic acid N-hydroxy-succinimide ester, β-maleimidobutyric acid N-hydroxysuccinimide ester, ε-maleimidocaproic acid N-hydroxysuccinimide ester, 4-(N-maleimidomethyl)-cyclohexane-1-carboxylic acid N-hydroxy-succinimide ester, 4-(N-maleimidomethyl-cyclohexane-1-carboxylic acid 3-sulfo-N-hydroxy-succinimide ester and β-maleimidopropionic acid N-hydroxysuccinimide ester.

Any antibody that is specific for a tumor cell surface marker is useful for the present invention. This antibody preferably has an affinity for a particular cell type that allows antibody targeting to deliver radioiodine for tumor imaging or for tumor therapy. Particularly preferred are internalizing pancarcinoma antibodies such as RS7 as described by Stein et al., Cancer Res. 50: 1330–36 (1990), internalizing lymphoma antibodies such as LL2 as described by Pawlak-Byczkowska et al., Cancer Res. 49: 4568–77 (1989) and anti-carcinoembryonic antigen antibodies such as Immu-14 as described by Hansen et al., Cancer 71: 3478–85 (1993). All three references are hereby incorporated by reference in their entirety. Also preferred are chimeric, humanized and human versions of antibodies and antibody fragments.

The present method is particularly well suited for coupling sulfhydryl-containing monovalent antibody fragments, e.g., Fab-SH or Fab'-SH, since they can be generated by reductive cleavage of divalent $F(ab)_2$ or $F(ab')_2$ fragments with an appropriate conventional disulfide reducing agent, e.g., cysteine, dithiothreitol, 2-mercaptoethanol, dithionite and the like. Reduction preferably is effected at pH 5.5–9.5, preferably 6.0–6.8, more preferably 6.1–6.4, e.g., in citrate, acetate or phosphate buffer, and advantageously under an inert gas atmosphere. Reduction is faster at higher pH, but reoxidation is also faster. An optimal pH is selected wherein reduction is reasonably rapid, but reoxidation, including the formation of mixed disulfides with thiol reducing agents, is negligible. Care must also be taken to avoid overly powerful reducing agents that will reduce light/heavy chain disulfide bonds in competition with heavy/heavy chain disulfide bonds within immunoglobulin proteins. Cysteine is preferred for such disulfide reductions but other thiols having similar oxidation potentials to cysteine also can be used. The ratio of disulfide reducing agent to protein is a function of interchain disulfide bond stabilities and must be. optimized for each individual case. Cleavage of $F(ab')_2$ antibody fragments is advantageously effected with 10–20 mM cysteine and a protein concentration of about 10 mg/ml.

Cleavage of divalent antibody fragments can be monitored by, for example, size exclusion HPLC, to adjust conditions so that Fab or Fab' fragments are produced to an optimum extent, while minimizing light-heavy chain cleavage. Eluate from a sizing gel column can be used directly or, alternatively, the Fab-SH or Fab'-SH solution can be kept at low temperature, e.g., in the refrigerator, for several days to several weeks, preferably at a pH of 3.5–5.5, more preferably at pH 4.5–5.0, and advantageously under an inert gas atmosphere, e.g., nitrogen or argon.

Optimum reaction conditions of time, temperature, ionic strength, pH and the like suitable for the coupling reactions of SCHEME 1, 2 and 3 can be determined by a minimum of experimentation. In fact, one principal advantage of the present invention is that the coupling reactions with maleimide and with substituted cyanuric dichloride can take place easily at neutral pH. Reaction temperature and ionic strength are likewise not critical. An important consideration is that non-extreme reaction conditions be chosen which will not denature the specific antibody used.

The invention is described further below by reference to illustrative examples.

EXAMPLES

Example 1

Preparation of (BOC)Gly-D-Tyr(O-t but)-D-Lys-OH

Fmoc-D-Lysine(Aloc) [0.325 g; 0.72 mmol] is dissolved in 5 ml of anhydrous dichloromethane ($CH_2Cl_2$), and mixed with 0.55 ml of diisopropylethylamine (DIEA). The solution is then added to 0.5 g of 2-chlorotrityl chloride resin in a 20 ml vial and the contents shaken vigorously for 18 h. The reddish slurry is placed in a column assembly fitted with a frit and a 3-way stopcock which can be used to either bubble nitrogen through the slurry for mixing purposes or for draining solution off the column and leaving the resin on the column. The solution is drained off, and the resin is washed with 3×40 ml of $CH_2Cl_2$:MeOH:DIEA (17:2:1), 3×40 ml of $CH_2Cl_2$, 2×40 ml of DMF, 2×40 ml of $CH_2Cl_2$ and 2×40 ml of MeOH. The resin is dried under a flow of nitrogen. The Fmoc group is cleaved by adding 40 ml of 5% piperidine in 1:1 (v/v) $CH_2Cl_2$-DMF for 10 minutes, draining the solution off, and continuing cleavage with 20% piperidine in $CH_2Cl_2$-DMF for 15 minutes. This is followed by a wash cycle with 40 ml DMF, 40 ml isopropanol(IPA), 40 ml NMP (N-methylpyrrolidone), 40 ml IPA and 4×40 ml NMP. The resin is then reacted with 1.8 mmol of activated Fmoc-D-tyrosine(O-t but) for 40 minutes. The activation is carried out using 0.827 g (1.8 mmol) of Fmoc-D-tyr(O-t but), 0.269 g of HOBT in 4 ml of NMP, adding to the clear solution 0.31 ml of diisopropylcarbodiimide (DIC), and keeping at ambient temperature for 20 minutes. After this period, 3.6 mmol (0.62 ml) of DIEA is added, and the reaction is continued for 25 minutes. The wash sequence, following Fmoc cleavage and subsequent wash sequence, are as described above. A second coupling using activated BOC-glycine (derived from 0.376 g or 3 mmol of Boc-glycine) is carried out in an analogous manner. The Aloc group is removed using a solution of 0.1547 g of tetrakis (triphenylphosphine) palladium(0) in a mixture of $CH_2Cl_2$ (40 ml): AcOH (2 ml) and DIEA (5 ml), followed by the addition of 5 ml of tributyltinhydride. After the usual wash sequence, the peptide is cleaved from the resin with 10 ml of acetic acid-trifluoroethanol-$CH_2Cl_2$ (1:1:8 v/v). The cleaved peptide solution is concentrated to 0.25 g of the title compound (gummy product). The product exhibits a single peak with a retention time of 7.10 min. on analytical reverse phase HPLC Electrospray mass spectrum shows the M+H peak at m/e 523 (positive ion mode) and the M–H at m/e 521 (negative ion mode).

Example 2

Preparation of Gly-D-Tyr-D-Lys (ITC-Bz-DTPA)-OH 9 0.053 g (0.1 mmol) of the product from step-1 is mixed with ITC-Bz-DTPA (81 mg of 80% DTPA content; 20% excess)in water-dioxane, and the pH is adjusted to 8.5. The solution is incubated for 2.5 h at 37° C. (bath). More ITC-DTPA (41 mg) is added, and the pH is readjusted to 8.56. The solution is then incubated for 2 h at the same temperature. Preparative HPLC purification on reverse phase column using a gradient elution of water (0.1%

TFA)/90% acetonitrile-water (0.1% TFA) furnishes 30 mg of (BOC)Gly-D-Tyr(O-tbut)-D-Lys(ITC-Bz-DTPA)-OH as a colorless solid. Analytical reverse phase HPLC shows a single peak with a retention time of 7.54 min. Mass spectrum analysis revealed a M+H peak at m/e 1063 (positive ion mode) and the M–H peak at m/e 1061 (negative ion mode). This material is then treated with a mixture of TFA/$CH_2Cl_2$/anisole for 1 h, and the BOC- and Tyr(O-t but) protecting groups are cleaved off. The title compound is precipitated by adding the reaction mixture to ethyl ether. The HPLC retention time was 5.31 min. Mass spectrum analysis showed AN M+H peak at 907, and AN M–H at 906.

Example 3

Preparation of (MCC)Gly-D-Tyr-D-Lys(ITC-Bz-DTPA)-OH 0.025 g (0.0138 mmol) of the product from Example-2 is dissolved in 0.5 ml of 0.1 M sodium phosphate pH 7.0. To this, 0.03 9 of commercially available sulfosuccinimidyl 4-(N-maleimidomethyl)-1-carboxylate (SMCC) is added and the pH is raised to 7.17. The clear solution is stirred for 1 h. Preparative HPLC on a preparative reverse phase column using the same gradient elution as in Example-1 yields 0.0054 g of the title compound [where MCC stands for the 4-N-maleimidomethyl)-1-carbonyl moiety]. The retention time of the purified material (analytical RP column) is 6.36 minutes. Electrospray mass spectrum analysis showed aN M+H peak at m/e 1126 and an M–H peak at m/e 1124.

Example 4

Radioiodination of Product From Example 3, Conjugations to a DTT-reduced Monoclonal Antibody IgG [LL2], and to a DTT-reduced Monoclonal Antibody IgG [RS7]

10 nanomoles of product of Example-3 is radioiodinated with 1.72 mCi of I-125-sodium iodide by an iodogen iodination method. The labeled substrate is transferred to a second vial, and treated with 60 nmol of 4-hydroxyphenylacetic acid, followed by reaction with 0.6 mg of an anti-lymphoma antibody [LL2] previously reduced with dithiothreitol to generate thiol groups by reduction of one or more interchain disulfide bonds of the antibody. After 1–2 h of reaction, the solution is made 5 mM in sodium tetrathionate, incubated for five minutes, and purified on a centrifuged size-exclusion column of Sephadex™ 50/80 in 0.1 M sodium phosphate pH 7. Based on the amount of activity placed on the column, a 37.4% recovery of radioactivity of antibody-bound material is obtained which was 95% pure as determined by size-exclusion chromatography via HPLC. The specific activity achieved in this procedure is 0.94 mCi/mg.

In a variation of this process, 10 nmol of the product of Example-3 is radioiodinated with 2.24 mCi of I-125 sodium iodide using chloramine T as oxidant for 1–2 minutes. Unused active iodine is quenched with 4-hydroxyphenylacetic acid, diluted with potassium iodide and reacted with 0.5 mg of DTT-reduced LL2 for 15–40 minutes. The work up and chromatography is as described above. This yields 41%–43% overall yield with a final specific activity in the 1.98–2.09 mCi/mg range.

The product of Example-3 (10 nmol) is radioiodinated with 1.46 mCi of NaI (I-125) using iodogen as oxidant, and the radioiodinated material is conjugated to DTT-reduced RS7 (0.5 mg). An overall yield (after purification) of 29.3% at a final specific activity of 1.0 mCi/mg is obtained. Analysis of the purified material on analytical SEC HPLC shows >98% of radioactivity associated with the antibody.

Example 5

In Vitro Binding Studies

The product of Example-4 is incubated with Raji cells ($10^6$ cells/ml in Dulbecco's double eagle medium) in a sterile incubator maintained at 37° C. After 2 h, the cells are pelleted by centrifugation, and the supernatant solution is discarded. The cells are washed three times with cold media. The washed cells are resuspended in fresh media and placed in an incubator. At various time points, a known volume of the cell suspension is removed, pelleted and the activity associated with the cell pellet is determined. The control experiment involves using the same antibody labeled directly by a chloramine T procedure (negative control) or the same antibody labeled with In-111 (by labeling the product of Example-3 with In-111 acetate, followed by coupling to DTT-reduced LL2 as a positive control) The product of Example-4 was found to be associated longer with the Raji cells by comparison with directly radioiodinated LL2. This retention parallels the retention of In-111 on Raji cells. [% initially bound cpm retained: For I-125 labeled LL2: 94.7% (2 h), 63.8 % (26 h), 51.1% (48 h)& 35.4% (120 h); for In-111 labeled LL2: 89.2% (2 h), 68.1 % (26 h), 49.8% (48 h) & 34.1% (120 h).

In a similar fashion, in vitro bindings, to Calu 3 non-small lung adenocarcinoma cell line, of RS7 radioiodinated with residualizing label of this invention (that is, the product of Example-3 radioiodinated and coupled to DTT-reduced RS7)and conventionally radioiodinated RS7 were compared. Data from this Example showed that the residualizing labe exhibited distinctly prolonged retention compared with that of the conventional iodine label.

Example 6

SCHEME IV Preparation of N,N-bis (Carboxymethyl)-N'-[2-(p-hydroxyphenyl)ethyl]-2-[p-isothiocyanatobenzyl]-ethylenediamine A and the Corresponding Maleimide B 4-Nitrophenylalanine is reduced with borane in THF. Reaction with two equivalents of tert-butylbromoacetate and anhydrous sodium carbonate in refluxing acetonitrile furnishes a dialkylated product in 67.9% yield after flash chromatographic purification. The 400-MHz proton ham NMR spectrum of this product is fully consistent with the structural assignment. The intermediate (0.1 g) is oxidized in high yield to aldehyde using DMSO/oxalyl chloride at –78° C. followed by treatment with triethylamine, and the purified product is reacted with tyramine in presence of sodium cyanoborohydride in aqueous methanol. This tyramine-appended intermediate (70% overall yield) is characterized by M+H peak at m/e 544 (electrospray mass spectrum, positive ion mode). Catalytic hydrogenation of the nitro group to an aniline derivative (product is characterized by mass spectrum), followed by a 2-step reaction sequence (involving deprotection of carboxyl protecting groups using hydrochloric acid, and a subsequent reaction with thiophosgene in 3 M hydrochloric acid) gives the isothiocyanate derivative A, which in turn is converted to maleimide derivative B in two steps (reaction with ethylenediamine, followed by treatment with SMCC as described in Example-3).

Example 7

Radioiodinations of Lymphoma Antibody (LL2) Using I-125-labeled A or I-125-labeled B (A & B of SCHEME-4)

Radioiodination of 10 nmol of A ($Na^{125}I$/iodogen) followed by quenching of unreacted radioiodine with 40 nmol of aqueous phenol, and subsequent reaction with 1.37 mg of LL2 at pH 8–8.2 for 3 h at 37° C. gives an incorporation of 32.8%. Experiments are carried out using lesser amounts of the antibody to increase the specific activity. An incorporation of 23.7% at a specific activity of 1.1 mCi/mg, and 24.1% incorporation at a specific activity of 1.4 mCi/mg are obtained. The aggregate content was as low as 2%. Using B, and reduced LL2 (reduction carried out as in Example-4), an incorporation of 28.4% at a specific activity of 0.95 mCi/mg is obtained, with negligible aggregation.

Example 8

Preparation of Dimelibiitoltyramine

The title product is prepared using 2.23 g (6.55 mmol) of melibiose, 0.089 g (0.657 mmol) of tyramine and 0.169 g (2.63 mmol) of sodium cyanoborohydride in 5 ml of borate buffer pH 9 at 65° C. for 18 h. The solution is acidified to pH 4.6, and purified on a 2.5 cm (o.d.) and 10 cm height column of Dowex 50-X2 cation exchange resin packed in 0.05 M ammonium acetate pH 4.6. Elution is with the same buffer, followed by a linear gradient of 1L of water and 1L of 1 M ammonium hydroxide at a flow rate of 2–3 ml/minute. Fractions of 4 ml each are collected. Assay of fractions by UV absorbance at 280 nm gave the elution profile. The elution profile contains a single peak. Accordingly, eluate fractions 60 through 70 are pooled, evaporated and lyophilized to obtain 0.98 g of a colorless solid comprising of the title product and an inorganic salt. The content of dimelibiitoltyrmine in an aqueous solution is determined using the absorbance value at 280 nm. The electrospray mass spectrum of the lyophilized material shows the correct M+H peak at m/e 790.

Example 9

Radioiodination of LL2 Using I-125-DMT

In one experiment, 10 nmol of DMT is labeled with I-125 (iodogen method). The iodinated DMT is then oxidized with about 10 units of galactose oxidase at 30° C. for 2.5 h. The oxidized $^{125}I$-DMT is reacted with equimolar (10 nmol) of LL2 and 20 mM sodium cyanoborohydride at the same temperature for 18 h. Incorporation is 18.7%, which is reproducible (20.7% in a second run).

Example 10

In Vitro Binding of Product of Example 9 to Raji Cells

The experiment is carried out analogously to that described in Example-5, using directly radioiodinated antibody (by a chloramine-T procedure) as a control. The results revealed significant retention, on Raji cells, of the product of Example-9 on Raji cells compared to that of the control over a 170 time period.

Example 11

SCHEME I: Reaction of Thiolated Antibody With a Maleimide-containing Hydrazide and Then With Oxidized Carbohydrate In the first step of this scheme, IgG disulfide bond(s) are reduced with dithiothreitol. Briefly, 0.55 ml of an internalizing anti-lymphoma antibody LL2 described by Pawlak-Byczkowska, et al., Cancer Research 49: 4568–77 (1989) is mixed with an equal volume of sodium phosphate buffer at pH 7.4, 0.11 ml of 0.5 M borate buffer pH 8.5 and 6 ul of 0.4 g/ml dithiothreitol in water. The reaction mixture is mixed vortex and incubated at room temperature for 30 minutes. The thiol reduced antibody is then purified by size-exclusion chromatography by passing the reduced protein solution through a Sephadex™ 50/80 resin equilibrated in phosphate buffer at pH 7.0.

In the second step of this scheme, a hydrazide group is introduced into the LL2. Ten equivalents of hydrazide-maleimide $M_2C_2H$ dissolved in dimethyl formamide are added to the prepared antibody solution for each SH group on the IgG. Incubation is continued at 37° C. for two hours. To quench the reaction, a 50-fold molar excess of N-ethylmaleimide is added and incubation is continued for another 30 minutes at 37° C. The treated IgG is then purified by size-exclusion chromatography.

In the third step of this scheme, IgG is conjugated with dimelibiitol-$^{125/131}I$-tyramine. Dimelibiitol tyramine is first radioiodinated with radioactive sodium iodide using iodogen. The iodinated dimelibiitol tyramine is oxidized with galactose oxidase by one of the procedures summarized by Strobel et al., Arch. Biochem. Biophys. 240: 635–45 (1985). The treated IgG is conjugated to the aldehyde group of oxidized dimelibiitol tyramine at a 1:1 molar ratio in phosphate buffer at pH 7.7. After two hours, sodium cyanoborohydride is added to a final concentration of 20 mM and the reaction mixture is incubated for an additional one hour. The conjugate that contains dimelibiitol-$^{125/131}I$-tyramine is again purified by size-exclusion chromatography at pH 7.4.

Example 12

SCHEME I: Thiolation of Antibody and Subsequent Coupling Via a Maleimide-containing Hydrazide In the first step of this scheme, at least one thiol group is introduced into an antibody by reaction with a thiolating reagent (1). The thiolating reagent is dissolved in dimethylformamide to a final dimethyl formamide concentration of 5% vol/vol. The thiol content of the prepared antibody is determined by Ellman's assay. The thiolated antibody is equilibrated in phosphate buffer at pH 7.5 and then allowed to react with a four-to ten-fold excess of the maleimide-hydrazide reagent $M_2C_2H$. After reaction between antibody and reagent MPBH, the conjugate is purified by size exclusion chromatography. The hydrazide-introduced antibody is then coupled to oxidized dimelibiitol-$^{123}I$-tyramine by following the procedures outlined in steps two and three of Example 11 above.

Example 13

SCHEME II: Introduction of a Maleimide-containing Hydrazide Into Oxidized Carbohydrate Followed by Coupling to Antibody In this scheme oxidized dilactitol-$^{123}I$-tyramine is incubated with a two-fold excess of $M_2C_2H$ in phosphate buffer between pH 6 and pH 7 for one hour. Then the thiolated antibody prepared as described above in Example 1 or Example 2 is added to the incubation mixture. After an additional 30 minutes of incubation at ambient temperature, iodoacetamide is added and incubated for another 30 minutes to quench unreacted thiol. Sodium cyanoborohydride is added to a final concentration of 10 mM and allowed to incubate for one hour. Prepared antibody is purified from the final reaction mixture by size exclusion chromatography.

Example 14

SCHEME III: Cyanuric Dichloride Coupling of Antibody With Residualizing Label

In this scheme a substituted cyanuric dichloride is used to couple antibody to residualizing label. The cyanuric dichloride derivative is dissolved in dimethyl formamide or in dimethyl sulfoxide and then added to a water solution of dilactitol-$^{123}$-tyramine.

In the case of coupling with a cyanuric dichloride analog, the cyanuric dichloride analog is first incubated with the residualizing label for 90 minutes at 37° C. After cooling, antibody solution in a phosphate buffer is added and the mixture is incubated for three hours at 37° C. The pH of the antibody buffer solution is adjusted so that the final reaction pH is between pH 7–8 when coupling to antibody. The final pH is between pH 6–7 for the case of coupling with thiolated antibody. The antibody is purified from other reactants by size exclusion chromatography.

For each of these examples, the conjugation efficiency is determined by measuring the amount of I-123 incorporated into protein and the amount of protein recovered. The degree of IgG aggregation is determined by molecular size analysis of prepared IgG using analytical size exclusion HPLC or polyacrylamide gel electrophoresis in the presence of sodium dodecyl sulfate.

The optimum amounts of residualizing agent, antibody and other reagents in these reactions are determined by varying their molar ratios and measuring the specific activities, binding affinities and amounts of conjugate formed under each reaction condition.

Example 15

Comparative Biodistributions of Lymphoma Antibody LL2, Labeled With Residualizing I125 Label Derived From Product of Example-3 or With I-131 Using Conventional Chloramine T method, in Nude Mice Bearing Ramos Human Tumor Xenografts Tumors were grown in 4-week old female nude mice using the Ramos tumor cell line. After two weeks tumor reach the size of about 0.1–0.2 gram. At this stage, groups of five mice were administered about 10 μCi each of the two iodine labels (I-125 residualizing & I-131 conventional), both contained in the same vial. The dual label gives the more precise comparisons since variations of antibody dose and tumor size do not exist. Animals are sacrificed at 1 day, 3 days, 5 days, 7 days and 10 days post-administration of the labeled antibody. Various organs including tumor are excised; the radioactivity associated with the organs are expressed as a percentage of injected dose per gram (% ID/g). Data obtained from this Example show prolonged retention and superior tumor:non-tumor ratios of accretion for residualizing I-125 label versus conventionally prepared (CT method) I-131 label.

From the foregoing descriptions, one skilled in the art can easily ascertain the essential characteristics of this invention and, without departing from the spirit and scope thereof, can make various changes and modifications of the invention to adapt it to various usages and conditions.

What is claimed is:

1. An aminopolycarboxylate-appended peptide useful for radioiodinating an antibody, comprising:

(a) a peptide that comprises at least one D-tyrosine or tyramine, an amino terminus, a carboxy terminus formed from a D-lysine and no contiguous L-amino acids between the D-tyrosine or tyramine and the carboxy terminus;

(b) an aminopolycarboxylate conjugated via one of its carboxylic acid groups to the peptide via an ε-amino group of the D-lysine to form an aminopolycarboxylate-appended peptide; and (c) a linker group for covalently binding said aminopolycarboxylate-appended peptide to an antibody.

2. The aminopolycarboxylate-appended peptide of claim 1, further comprising a radioiodine atom covalently bound to the D-tyrosine or tyramine residue.

3. The aminopolycarboxylate-appended peptide of claim 1, wherein said linker is capable of reacting with a sulfhydryl residue of an antibody to form a covalent bond.

4. The aminopolycarboxylate-appended peptide of claim 1, wherein said peptide contains 5–40 amino acids.

5. The radioionated aminopolycarboxylate-appended peptide of claim 2, wherein said peptide contains 5–40 amino acids.

6. The aminopolycarboxylate-appended peptide of claim 1, wherein said tyramine or D-tyrosine is directly linked to said D-lysine.

7. The aminopolycarboxylate-appended peptide of claim 1, wherein said aminopolycarboxylate is selected from the group consisting of nitrilotriacetic acid, EDTA, DTPA, TTHA and backbone-substituted derivatives of nitrilotriacetic acid, EDTA, DTPA and TTHA.

8. The aminopolycarboxylate-appended peptide of claim 1, wherein said linker is selected form the group consisting of an amino group, imidate group, isothiocyanate group, maleimide group and halo-acetamide group.

9. An aminopolycarboxylate-appended peptide useful for radioiodinating an antibody, comprising:

(a) a peptide that comprises at least one D-tyrosine or tyramine, an amino terminus, a carboxy terminus formed from a D-amino acid and no contiguous L-amino acids between the D-tyrosine or tyramine and the carboxy terminus;

(b) an aminopolycarboxylate conjugated via one of its amino groups to the peptide via an amide bond to a peptide carboxylic acid group or via a thiourea bond to a peptide amino acid residue to form an aminopolycarboxylate-appended peptide; and (c) a linker group for covalently binding said aminopolycarboxylate-appended peptide to an antibody.

10. The aminopolycarboxylate-appended peptide of claim 9, wherein said aminopolycarboxylate is selected from the group consisting of nitrilotriacetic acid, EDTA, DTPA, TTHA and backbone-substituted derivatives of nitrilotriacetic acid, EDTA, DTPA and TTHA.

11. The aminopolycarboxylate-appended peptide of claim 9, wherein said linker is selected form the group consisting of an amino group, imidate group, isothiocyanate group, maleimide group and halo-acetamide group.

* * * * *